United States Patent [19]

Alleluia

[11] Patent Number: 4,562,882
[45] Date of Patent: Jan. 7, 1986

[54] METHOD OF MAKING A DENTAL PROSTHESIS

[76] Inventor: Vincent V. Alleluia, 146-21 - 13th Ave., Whitestone, N.Y. 11357

[21] Appl. No.: 584,644

[22] Filed: Feb. 29, 1984

[51] Int. Cl.⁴ .................. B22C 1/00; B22D 23/00
[52] U.S. Cl. .................................. 164/529; 164/46; 264/16; 264/222; 264/338; 433/171; 433/200.1; 433/214
[58] Field of Search ............... 264/16, 17, 222, 338; 433/214, 200, 171; 164/19, 33, 34, DIG. 4, 459, 46, 529

[56] References Cited

U.S. PATENT DOCUMENTS

| | | | |
|---|---|---|---|
| 411,538 | 9/1889 | Stedman | 433/214 X |
| 422,165 | 2/1890 | Stedman | 433/214 X |
| 1,930,119 | 1/1934 | Bayes | 433/200 X |
| 1,961,626 | 6/1934 | Touceda | 433/200 X |
| 2,106,809 | 2/1938 | Prange et al. | 433/200 |
| 2,250,246 | 7/1941 | Axline et al. | 164/19 X |
| 2,289,262 | 7/1942 | Groean | 164/19 |
| 2,293,062 | 8/1942 | Ingham | 164/19 X |
| 2,423,330 | 7/1947 | Levine | 164/DIG. 4 |
| 2,629,907 | 3/1953 | Hugger | 164/46 X |
| 2,798,294 | 7/1957 | Zahn | 433/170 |
| 2,966,423 | 12/1960 | Shichman | 164/46 X |
| 3,023,500 | 3/1962 | Prosen | 433/170 |
| 3,077,647 | 2/1963 | Kugler | 164/19 |
| 3,182,361 | 5/1965 | Trimble | 164/46 X |
| 3,192,583 | 7/1965 | Fryrear, Jr. | 164/34 |
| 3,649,732 | 3/1972 | Brigham et al. | 264/16 X |
| 3,663,141 | 5/1972 | Clenet et al. | 164/34 X |
| 4,141,405 | 2/1979 | Spindt | 164/46 |

FOREIGN PATENT DOCUMENTS

| | | | |
|---|---|---|---|
| 1919652 | 11/1970 | Fed. Rep. of Germany | 433/200.1 |
| 1394624 | 5/1963 | France | 163/33 |
| 2301607 | 9/1976 | France | 264/16 |

OTHER PUBLICATIONS

Raymond, E. H., Lieut. "A Type of Denture for Army Use" in *Dental Cosmos*, 1918, pp. 516–519.
Phillips, Ralph W. *Skinner's Science of Dental Materials* 8th Edition, W. B. Saunders Co., 1982, pp. 406, 407 and 408.
Kornfeld, Max *Mouth Rehabilitation* vol. II, C. V. Mosby Co., 1974, pp. 495, 496.
Air Force Manual 162-6 *Dental Laboratory Technology*, Jan. 22, 1975, p. 8-2.

*Primary Examiner*—Philip Anderson
*Attorney, Agent, or Firm*—Paul W. Garbo

[57] ABSTRACT

A method of making a dental prosthesis includes providing an upper or a lower impression of the oral cavity of a patient; and filling such impression with a castable mixture comprising (1) a ceramic composition containing a major proportion of magnesia and a significant minor proportion of alumina and (2) an aqueous composition containing silica as the essential ingredient, the ratio of the aqueous silica composition to the ceramic composition being such as to render the latter flowable. The mixture is then permitted to harden in the impression, and the resulting hardened model is removed from the impression. Thereafter, a liquefied metal composition is spray-coated on to a selected portion of the model to form a metallic prosthetic base, which is separated from the selected portion of the model and provided with a porcelain coating on its exterior surface.

7 Claims, 2 Drawing Figures

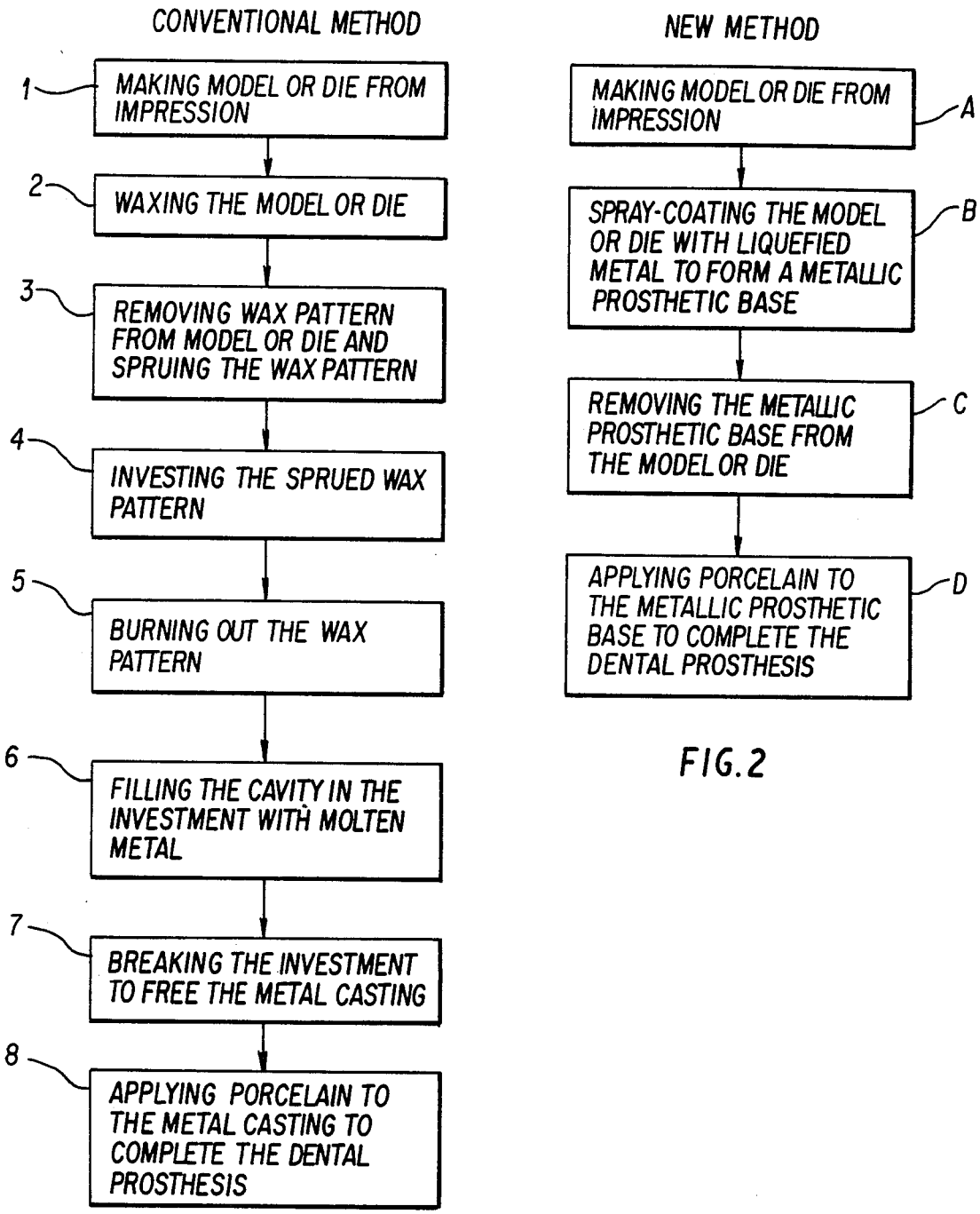

4,562,882

METHOD OF MAKING A DENTAL PROSTHESIS

BACKGROUND OF THE INVENTION

This invention relates to the preparation of dental prostheses and more particularly to the provision of a metal-substrate dental prosthesis.

A dental restoration such as a cap or crown generally comprises a metal frame or substate, the external surface of which is coated with porcelain appropriately matching the capped or crowned tooth as well as the adjoining teeth. In the production of such a dental restoration, the decayed and/or damaged portion of the tooth is suitably removed by the dentist for reception of the desired cap or crown. Thereafter an impression is taken of such prepared tooth so that the required metal base or substrate can be formed.

The procedure generally utilized in preparing such a restoration involves the use of the so-called "lost wax technique". Upper and lower impressions of the patient's oral cavity are customarily made, for which purpose any of the usual moldable impression materials may be employed. A model or die of each impression is then made by filling the respective impression with an aqueous slurry of a gypsum or similar calcium sulfate material, and permitting the gypsum material to dry and harden. The resulting models are then removed from the respective impressions and are mounted on an articulator in a manner such that the teeth on the two models are in the same relative position as the teeth in the patient's mouth. It will be appreciated, of course, that the impressions are negatives of the patient's upper and lower tooth structures.

In this manner the conditions existing in the patient's mouth are reproduced, whether an upper or a lower restoration is required. In either case a wax pattern of the crown to be fabricated is now made by applying wax to at least the model area or areas including the missing tooth portion or portions. The net effect is that the inside surface of the resulting wax pattern matches the prepared surface of the tooth to be restored, while the outer surface of the wax pattern is shaped to fit the adjacent teeth.

The wax pattern is then removed from the model or models and invested or placed in a refractory ceramic material that has a flowable consistency such that it fills and surrounds the wax pattern. A wax sprue is formed on the pattern to provide a passage through which the subsequently vaporized wax can escape and through which the molten metal can be introduced to form the desired metal substrate. The refractory ceramic material is one that has been specially formulated to withstand the thermal shock that occurs upon sudden exposure of the same to molten metal at a high temperature.

The refractory ceramic material filling and surrounding the wax pattern is now permitted to dry and harden, whereupon heat is applied to the combination to raise its temperature to a point sufficiently high that the wax is melted and vaporized, the vaporized wax escaping through the opening formed by the sprue. There thus results a cavity mold comprising a negative replica of the crown or other restoration desired, the inside of such cavity mold corresponding to the prepared surface of the tooth to be capped.

Generally, the resulting refractory ceramic material mold is mounted in a centrifugal casting machine. The desired metal composition is then heated to melt the same; and the molten metal is poured into the cavity mold to the desired extent. Cooling and solidification of the molten metal then take place; and finally the ceramic material mold is broken away from the resulting cast crown.

Cleaning and polishing of the rough cast crown follow, together with the fitting of such crown to the prepared tooth and correction of the crown as necessary to provide a proper fit. Usually a porcelain coating is desired; and an appropriate porcelain composition is applied to the exterior of the metal crown and heat-treated in the customary manner. Finally, the finished crown is cemented in place on the prepared tooth.

Although a satisfactory metal base or substrate can be obtained by this "lost wax technique", it has been recognized that this procedure is not only laborious and technique-sensitive but is time-consuming and thus costly. Usually, at least six hours are required to produce the metal base from the impression as received from the dentist. In addition, application of the porcelain coating to the metal base involves upwards of another four hours.

Various modifications of such "lost wax technique" have been proposed from time to time. For one reason or another, however, none of these proposals has been particularly effective especially in decreasing the time required to prepare the metal coping or substrate or in materially reducing the technique-sensitivity of the restoration procedure. Thus, despite its drawbacks, this "lost wax technique" has remained as the conventional procedure for preparing a dental restoration.

SUMMARY OF THE INVENTION

It has now been found that the disadvantages of the "lost wax technique" can be substantially avoided by directly forming a refractory die or model from the impression, and entirely eliminating the use of a wax. To accomplish this objective, there is utilized a castable refractory composition containing a major proportion of magnesia and a significant minor proportion of alumina to form a refractory die or model capable of withstanding the temperature of liquefied metal to be sprayed thereon.

To facilitate understanding of the method of this invention and the resulting substantial advance in the art of making a dental prosthesis, appended FIG. 1 presents a flow diagram of the steps in the conventional method and FIG. 2 presents a flow diagram of the fewer and simpler steps in the new method. Both flow diagrams tersely identify the procedural steps. Step 1 of FIG. 1 and Step A of FIG. 2 involve the same starting operation and differ only in the composition used to make the model or die. Steps 2,3,4 and 5 of FIG. 1 are eliminated by the new method of FIG. 2. Steps B and C of FIG. 2 replace steps 6 and 7 of FIG. 1, while step D is the same as step 8.

DESCRIPTION OF THE PREFERRED EMBODIMENT

In the carrying out of this new procedure, an upper or a lower impression of the oral cavity of a patient is made in the customary manner. For this purpose, as is well known, any of various moldable plastic materials such as a silicone resin is employed. The impression, of course, is made by the patient's dentist, who then sends it on to a dental technician for preparation of the desired restoration.

The impression is then filled with a castable mixture comprising (1) a ceramic composition containing a major proportion of magnesia and a significant minor proportion of alumina as well as of ammonium dihydrogen phosphate, and (2) an aqueous composition containing silica as the essential ingredient. The amount of the aqueous silica composition combined with the ceramic composition may vary but must be sufficient to render the latter flowable. Generally, such castable mixture comprises by weight about 3 to 5 parts of the ceramic composition to 1 parts of the aqueuos silica composition, the ratio advantageously being about 3:1.

Prior to filling the impression with the castable mixture, it is desirable to coat the impression with a wetting agent in order to reduce any surface tension effects. Any well-known wetting agent may be utilized for this purpose. A particularly suitable wetting agent is an aqueous solution of sodium di-octyl-sulfosuccinate.

The castable mixture is permitted to harden or set in the impression and is then removed therefrom to provide the basic die or model. Such model is then preferably dried by heating the same to a temperature and for a time sufficient to effect the desired drying. Generally, the model is heated to a temperature on the order of 400° F. for a time on the order of 20 minutes, whereafter it is permitted to cool. Such drying can be readily effected in any suitable kiln.

The model is now ready for spray-coating with a liquefied metal composition. Prior to such spray-coating, a parting agent is preferably applied to at least a selected portion and generally all of the model in order to assist in the release of the resulting metal substrate therefrom. Any well-known parting agent may be employed for this purpose. One that is especially suitable comprises an appropriate silicone resin and/or an acrylic resin in an organic liquid carrier, the resin including a small amount of carbon and a metal alloy.

The so-treated model or die is now preheated in preparation for the application of the liquefiable metal composition, which may be in powdered or wire form, depending on the type of spray-coating device that is employed. Usually the metal composition is utilized as a powder, which is introduced into a spray gun capable of producing a temperature sufficiently high to melt the powder and to project the resulting molten metal at a high velocity against the area of the external model surface to be coated. Such spray-coating is continued until a metallic prosthetic base of the desired thickness, generally on the order of about 0.5 to 1 mm. is formed. The outer surface of the resulting metallic prosthetic base as a nodular effect, which assists in the mechanical retention of the porcelain finish customarily applied thereto.

Upon completion of the spraying operation, the coated model is then cooled to room temperature; and the resulting metallic prosthetic base is removed from the model. Following any appropriate cleaning or other preliminary preparation of the separated metallic prosthetic base, a porcelain coating of the desired thickness is then applied to the exterior surface of such prosthetic base in the usual manner to provide a porcelain-coated metallic-substrate dental prosthesis. In the event that a metallic dental prosthesis is preferred, additional metal is applied to the exterior surface of the substrate to the extent necessary.

The time required to produce the metallic prosthetic base from the impression as received from the dentist is about one hour. It will thus be seen that the present procedure possesses a more than considerable time advantage over the "lost wax technique". Of this total time only about five minutes or so are needed to spray-coat the liquefied metal composition on to the prepared die or model.

As indicated above, the castable mixture comprises (1) a magnesia-alumina ceramic composition and (2) an aqueous silica composition. The magnesia and the alumina are present in the ceramic composition in a weight ratio ranging between about 1.25:1 to about 6:1, a preferred weight ratio being about 1.4:1. The aqueous silica composition generally comprises about 40% to about 60% silica by weight, about 50% silica by weight being preferred.

The preferred ceramic composition comprises the following ingredients in percent by weight:
Magnesia: 54.15
Alumina: 38.25
Ammonium dihydrogen phosphate: 5.00
Calcium oxide: 0.84
Silica: 0.75
Trace elements including water: 1.01

The ratio of magnesia to alumina is about 1.4:1 by weight.

Another suitable ceramic composition comprises basically the following in parts by weight:
Magnesia: 100
Alumina: 40
Ammonium dihydrogen phosphate: 20

Here the ratio of magnesia to alumina is 2.5:1 by weight.

A further suitable ceramic composition comprises basically the following in parts by weight:
Magnesia: 120
Alumina: 20
Ammonium dihydrogen phosphate: 20

Here the ratio of magnesia to alumina is 6:1 by weight.

Use of the magnesia and the alumina within the indicated ranges provides a model having satisfactory thermal expansion characteristics, exhibiting little or no distortion at the elevated temperatures encountered during spray-coating of the liquefied metal composition, and possessing suitable hardness and strength to adequately resist cracking and spalling during the spray-coating operation. As a result, there is obtained a metallic prosthetic base having properties equal or superior to those of a metallic prosthetic base produced by the "lost wax technique" in approximately one-sixth the time.

The preferred aqueous silica composition comprises the following ingredients in percent by weight:
Silica: 50.45
Trace oxides (sodium oxide, alumina, iron oxide, magnesia): 0.184
Water: Balance The silica content, as is apparent, is about 50% by weight.

The purpose of the aqueous silica composition, as indicated above, is to convert the magnesia-alumina ceramic composition, which is normally in powdered form, into a mixture that can be suitable cast into the impression. The resulting castable mixture or slurry can be readily introduced into the impression and will result in a shaped die or model upon the above-indicated heating and drying operation.

If desired, the ceramic composition may be impregnated or mixed with a metal powder to improve the heat conductivity of the resulting model. Such an impregnated ceramic composition may comprise 95 to 50% of the ceramic composition and 5 to 50% of the metal powder by weight respectively. The powdered metal may comprise copper, a bronze, or a nickel-chromium alloy.

The liquefied metal composition that is spray-coated on to the model may comprise any alloy appropriate for the intended purpose. Such composition may comprise a nickel-chromium alloy such as one having the following composition in percent by weight:
Chromium: 9
Aluminum: 7
Molybdenum: 5.5
Iron: 5
Nickel: Balance A suitable nickel-aluminum alloy comprises the following ingredients in percent by weight:
Aluminum: 4
Nickel: Balance In place of the parting agent, a burnishable metal foil may be applied to the model before spray-coating the same with the liquefied metal composition. Such a metal foil may be formed of nickel, palladium, or platinum and is burnished in place on the model in order to pick up the detail thereof. Once the liquefied metal composition has been spray-coated on to the foil-covered model and the resulting combination has been cooled, the metallic prosthetic base is separated from the model and the foil.

The present procedure is also applicable to the formation of a bridge including two or more dental restorations. It can also be utilized in the production of partial and complete dentures.

I claim:

1. A method of making a dental prothesis from an upper or a lower impression of the oral cavity of a patient, which comprises filling said impression with a castable mixture comprising (1) a ceramic composition containing a major proportion of magnesia and a significant minor proportion of each of alumina and ammonium dihydrogen phosphate, and (2) an aqueous composition containing silica as the essential ingredient, the ratio of the aqueous silica composition to the ceramic composition being such as to render the latter flowable; permitting said mixture to harden in the impression, and removing the resulting hardened model from the impression; selecting from said model the portion requiring said dental prosthesis, effecting drying thereof, and spray-coating a liquefied metal composition on to said selected portion of said model to form a metallic prosthetic base; and separating said metalic prosthetic base from said selected portion of said model and applying a porcelain coating to the exterior surface of said separated metallic prosthetic base to provide said dental prosthesis.

2. A method according to claim 1, in which the castable mixture comprises by weight about 3 to 5 parts of the ceramic composition to 1 part of the aqeuous silica composition.

3. A method according to claim 1, in which the magnesia and the alumina in the ceramic composition are present in a ratio between about 1.25:1 and about 6:1 by weight, and said ceramic composition contains at least 5% by weight of ammonium dihydrogen phosphate.

4. A method according to claim 1, in which the aqueous silica composition comprises about 40% to about 60% silica by weight.

5. A method according to claim 1, in which the liquefied metal composition comprises a nickel-chromium alloy.

6. A method according to claim 1, in which the liquefied metal composition comprises a nickel-aluminum alloy.

7. A method of making a dental prosthesis from an upper or a lower impression of the oral cavity of a patient, which comprises filling said impression with a castable mixture comprising (1) a ceramic composition containing magnesia and alumina in a ratio of about 1.4:1 by weight and about 5% by weight of ammonium dihydrogen phosphate, and (2) an aqueous composition containing about 50% silica by weight, the ratio of the ceramic composition to the aqueous silica composition being about 3:1 by weight: permitting said mixture to harden in the impression, and removing the resulting hardened model from the impression; heating the model to a temperature on the order of 400° F. for about 20 minutes, and then cooling the same; selecting the portion of the model requiring said dental prosthesis and spray-coating a liquified metal composition on to said selected portion for a time to form a metallic prosthetic base having a thickness of about 0.5 to 1 mm; cooling the spray-coated selected portion and separating the metallic prosthetic base therefrom; and applying a porcelain coating to the exterior surface of said metallic prosthetic base to provide said dental prosthesis.

* * * * *